US011795489B2

(12) United States Patent
Thomas et al.

(10) Patent No.: US 11,795,489 B2
(45) Date of Patent: Oct. 24, 2023

(54) LOW CROSS-LINKING GELATINE

(71) Applicant: Rousselot B.V., Son (NL)

(72) Inventors: Pierre-Albert Marie Thomas, Son (NL); Claude Françoise Capdepon, Son (NL); Ellen Leona Gabriël Verwee, Son (NL); Catherine Emmanuelle Thérèse Baron, Son (NL)

(73) Assignee: Rousselot B.V., Son (NL)

( * ) Notice: Subject to any disclaimer, the term of this patent is extended or adjusted under 35 U.S.C. 154(b) by 1239 days.

(21) Appl. No.: 16/319,679

(22) PCT Filed: Jul. 24, 2017

(86) PCT No.: PCT/NL2017/050500
§ 371 (c)(1),
(2) Date: Jan. 22, 2019

(87) PCT Pub. No.: WO2018/016962
PCT Pub. Date: Jan. 25, 2018

(65) Prior Publication Data
US 2020/0377924 A1 Dec. 3, 2020

(30) Foreign Application Priority Data
Jul. 22, 2016 (NL) .................... 2017219

(51) Int. Cl.
C12P 21/06 (2006.01)
A61K 9/48 (2006.01)

(52) U.S. Cl.
CPC ............ *C12P 21/06* (2013.01); *A61K 9/4825* (2013.01); *C12N 2533/54* (2013.01); *C12Y 304/21067* (2013.01)

(58) Field of Classification Search
None
See application file for complete search history.

(56) References Cited

U.S. PATENT DOCUMENTS

| 5,919,906 | A | 7/1999 | Rowlands et al. |
| 6,080,843 | A | 6/2000 | Rainville et al. |
| 10,364,283 | B2 * | 7/2019 | Oesser .................... A23J 3/342 |
| 2004/0202948 | A1 | 10/2004 | Honan et al. |

FOREIGN PATENT DOCUMENTS

| CN | 101151300 A | 3/2008 |
| DE | 285 255 A7 | 12/1990 |
| EP | 0100052 | 2/1984 |
| EP | 0100052 A1 | 2/1984 |
| GB | 836082 * | 6/1960 |
| GB | 836082 A * | 6/1960 |
| WO | 01/34646 | 5/2001 |
| WO | WO 01/34646 A2 | 5/2001 |
| WO | 2004/091317 | 10/2004 |
| WO | WO 2004091317 A1 | 10/2004 |
| WO | 2014/040921 | 3/2014 |
| WO | WO 2014040921 A1 | 3/2014 |

OTHER PUBLICATIONS

International Search Report, International Patent Application No. PCT/NL2017/050500, dated Oct. 30, 2017, 4 pages.
G. Reich: "Formulation and physical properties of soft capsules", Pharmaceutical Capsules, 2nd edition, Ch. 11, 2004, pp. 201-212.
R. Schrieber and H. Gareis: "From Collagen to Gelatine", Gelatin Handbook, Chapter 2, 2007, pp. 45 to 117.
Davis et al., Kinetic study of the crosslinking of gelatin by formaldehyde and gloyoxal. Journal of Polymer Science: Part A, vol. 1 (1963) 799-815.
Hill. "The literature of gelatin", Chapter 20 of "literature of chemical technology", Washington D.C., 1968.
International Search Report for PCT/NL2017/050500. dated Oct. 30, 2017. 4 pages.
Moll et al., The structure of gelatin crosslinked with formaldehyde. The Journal of Photgraphic Science, vol. 22, 1974. pp. 255-261.
Podczek: Pharmaceutical Capsules, 2nd edition. 2004.TOC only. 7 pages.
Robinson. "Rate of crosslinking of gelatin in aqueous solutions", Journal of Applied Polymer Science 8 (1964) 1903-1918.
Schacht et al., Some aspects of the crosslinking of gelatin by dextran dialdehydes. Polymer Gels and Networks 1 (1993) 213-224.
Zezhou Man. Influence of Inorganic Salts on Performance of Fish Scale Gelatine Gel, Full-text Database of Chinese Excellent Theses for Master Degree (Electronic Journal), Issue 2, 2015, pp. B024-52.

* cited by examiner

Primary Examiner — Nghi V Nguyen
(74) Attorney, Agent, or Firm — CASIMIR JONES, SC; Robert A. Goetz

(57) ABSTRACT

The present invention relates to a process for the preparation of a gelatine blend comprising the steps of a) providing a gelatine extract or a series of gelatine extracts, differing in bloom and viscosity; b) subjecting a portion of one or more of the gelatine extracts of a) to an enzymatic treatment to obtain one or more enzymatically treated extracts having a viscosity that is lower than that of the respective extract before said enzymatic treatment, while maintaining the bloom substantially unaffected, the enzymatically treated extracts comprising less than 1.5 w/w % of gelatine-derived peptides having a molecular weight of less than 2000 Da; c) selecting one or more gelatine extracts of step a); d) combine the selected one or more gelatine extracts of step c) and blend with one or more enzymatically treated extracts of step b) to provide a gelatine composition having a lower viscosity as compared to that of the said combined selected extracts of step c) without being blended with said selected one or more enzymatically treated gelatine extracts of step b), while maintaining the bloom substantially unaffected. The present invention also relates to a gelatine composition, and a gelatine product comprising said gelatine composition.

19 Claims, 2 Drawing Sheets

LOW CROSS-LINKING GELATINE

FIELD OF THE INVENTION

The present invention relates to a process for the preparation of a gelatine composition, to gelatine compositions, and to a gelatine product comprising a gelatine composition according to the invention.

BACKGROUND

Gelatine is widely used in the pharmaceutical and nutraceutical fields for the manufacture of capsules. Capsules are solid dosage forms in which a drug substance and/or excipients are enclosed within a soluble container or shell or coated on the capsule shell. The shells may be composed of two pieces (a body and a cap), or they may be composed of a single piece.

Two-piece capsules are commonly referred to as hard-shell capsules, and one-piece capsules are often referred to as soft-shell capsules. Two-piece capsules consist of two telescoping cap and body pieces in a range of standard sizes.

One-piece capsules typically are used to deliver a drug substance as a solution or suspension. Liquid formulations placed into one-piece capsules may offer advantages by comparison with dry-filled capsules and tablets in achieving content uniformity of potent drug substance(s) or acceptable dissolution of drug substance(s) with poor aqueous solubility.

Soft gelatine capsules are filled with a liquid or semi-liquid fill surrounded by a single gelatine shell. A problem encountered in with soft gelatine capsules is the stability of the gelatine shell. In many cases, the filling of the capsule is such that it can react with the free functional groups of gelatine, including the amine groups of the amino acids which form the backbone of the protein, the shell becomes hard and brittle, and can even crack. Consequently, its solubility and dissolution in gastric and aqueous media decreases which is, particularly in the case of pharmaceutical applications, a major drawback.

Alternatively, on prolonged storage self-crosslinking of the gelatine shell can occur. Such cross-linking can occur in hard gelatine capsules. In this case, oxidation of the lysine side residues present in the gelatine leads to aldol condensation forming cross-links within the gelatine shell.

Various solutions have been proposed to avoid self-crosslinking and fill cross-linking. EP 121321 A1, discloses the use of a mixture of gelatine, sorbitol and sorbitan to form the envelope of soft capsules which contain polyethylene glycol as liquid carrier, to suppress embrittlement of the capsule during storage.

FR 2617047 discloses gelatine capsules, resistant to tanning (cross-linking) by the encapsulated products, characterized in that the gelatine contains an ammonium derivative and/or a sulphite derivative. A delay in cross-linking is only shown for gelatine having a bloom of between 242 and 266 g which is less suitable for use in soft gelatine capsules.

WO 03/103582 discloses compositions and methods for reducing cross-linking in the gelatine sell of a gelatine capsule by incorporation of free amino acid into the capsules shell and by inclusion of a carboxylic acid ester in to the capsule filling, and/or capsule shell and/or into the lubricant agent, and combinations thereof.

WO 2006/128685 discloses a low molecular weight gelatine hydrolysate that, when blended with higher molecular weight hydrolysates, reduces the gelatine's cross-linking and improves dissolution properties by increasing the free glycine, or other amino acids and small peptides, in the blended gelatine product.

A common feature of WO 03/103582 and WO 2006/128685 is that the disclosed methods require the addition of free amino acids or gelatine hydrolysate to the gelatine. A disadvantage of the addition of such low molecular weight components is that the elasticity of the gelatine may be adversely affected, leading to difficulties in the processing of such a gelatine.

In the art, it is known that crosslinking coincides with the viscosity of the gelatin. The higher the viscosity, the more crosslinking is observed, which is undesirable as discussed above. It is known in the art to prepare series of extracts, wherein the bloom and viscosity of each of the extracts of the series differ from one another. In the art, it is known to blend these extracts in order to arrive at an envisaged viscosity. However, by this blending, the bloom value of the blend is affected accordingly, whereas it is desired to lower the viscosity to a much higher extent than the bloom value. The blends of the art may have the desired viscosity, but the bloom value of such blends is unacceptably low.

It is an aim of the present invention to provide a gelatine composition that has good processability.

It is an aim of the present invention to provide a gelatine composition that exhibits reduced cross-linking.

It is an aim of the present invention to provide a gelatine capsule that has improved stability on storage.

SUMMARY

The present invention relates to a process for the preparation of a gelatine composition, to gelatine compositions, and to a gelatine product comprising a gelatine composition according to the invention.

DETAILED DISCUSSION

Figure 1:
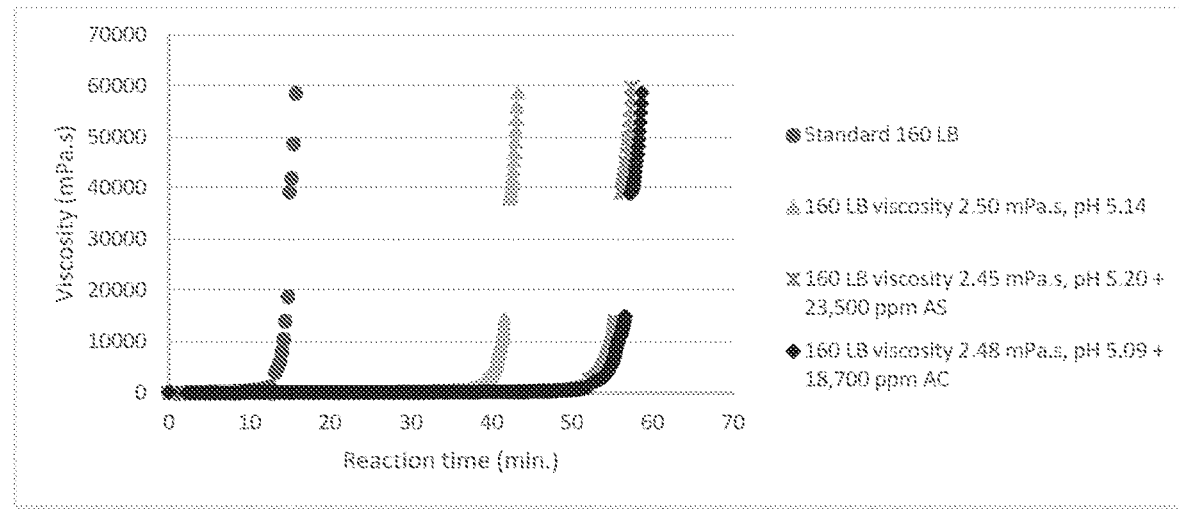
FIG. 1: Results of the cross-linking test for standard type B bovine bone gelatine having a bloom of 160 g (160 LB) having viscosity of 3.70 mPa·s and a pH of 5.73 (circles) compared with an improved type B bovine bone gelatine having a bloom of 160 with lower viscosity of 2.50 mPa·s and a lower pH of 5.14 (triangles), and with the improved 160 LB gelatine combined with the addition of 23,500 ppm ammonium sulphate (AS) having a viscosity of 2.45 mPa·s and a pH of 5.20 (crosses) and with the improved 160 LB gelatine combined with the addition of 23,500 ppm ammonium chloride (AC) having a viscosity of 2.48 mPa·s and a pH of 5.09 (diamonds).

It has been found that the drawbacks of the prior art can be overcome by preparing a gelatine blend, according to a process comprising the steps of:

a) providing a gelatine extract or a series of gelatine extracts, differing in bloom and viscosity, b) subjecting a portion of one or more of the gelatine extracts of step a) to an enzymatic treatment to obtain one or more enzymatically treated extracts having a viscosity that is lower than that of the respective extract before said enzymatic treatment, while maintaining the bloom substantially unaffected, the enzymatically treated extracts comprising less than 1.5 w/w % of gelatine-derived peptides having a molecular weight of less than 2000 Da, c) selecting one or more gelatine extracts of step a), d) combine the selected one or more gelatine extracts of step c) and blend with one or more enzymatically treated extracts of step b) to provide a gelatine composition having a lower viscosity as compared to that of the said combined selected extracts of step c) without being blended with said selected one or more enzymatically treated gelatine extracts of step b), while maintaining the bloom substantially unaffected.

In first step a), a single gelatine extract having a specific bloom and viscosity is provided, or a series of extracts of which the extracts differ in bloom and viscosity. In the art, the preparation of such a gelatine extract or such a series of extracts is known. In step b), a portion of the single gelatine extract, or, when a series of extracts is provided in step a), one or more of the said extracts is enzymatically treated such, that the bloom value of the treated extract is substantially maintained, while the viscosity is reduced as compared to the non-treated extract. By combining the one or more enzymatically treated extracts with one or more of the non-treated extracts of step a), which are selected in step c), a gelatine blend can be obtained wherein the viscosity is reduced, while the bloom value is substantially unaffected as compared to the same extract or combination of extracts without being blended with the one or more enzymatically treated extracts. By this method, combinations of extracts and enzymatically treated extracts can be made resulting in gelatine blends having the envisaged low viscosity while having a higher bloom as compared to those known in the art. Such blends are very advantageous in the preparation of gelatine capsules.

In an attractive embodiment, step a) of the process according to the present invention comprises the preparation of a series of extractions, wherein:

i. a first extraction step results in a first gelatine extract having a first viscosity and a first bloom, followed by, ii. a subsequent second extraction step resulting in a second additional gelatine extract having a second viscosity and a second bloom, optionally followed by, iii. one or more subsequent additional extraction steps, each resulting in a subsequent additional gelatine extract having a subsequent viscosity and a subsequent bloom, wherein the viscosity and the bloom of each subsequent gelatine is preferably less than that of the preceding extract.

As outlined above, the extraction process can provide a single gelatine extract having a specific bloom and viscosity. In that case, a portion of the said extract is enzymatically treated and combined with a portion of the untreated extract, resulting in a gelatine blend having a lower viscosity than of the non-treated extract while having substantially the same bloom value. The proportions of the untreated extract and the treated extract in the blend can vary, depending on the envisaged viscosity. The lower the envisaged viscosity, the higher the proportion of the enzymatically treated extract in the blend is. Attractively, however, the process has at least a first and a second extraction step, resulting in a first and second extract having different bloom and viscosity. According to the invention, the first or second extract, or both, are subjected to an enzymatic treatment, and the said treated extract or extracts can be combined with the first or second non treated extract or both, to arrive at a gelatine blend having the envisage high bloom value and reduced viscosity. If both the first and second extracts are to treated enzymatically, the extracts can be treated separately or can be combined before treatment. It is also possible in a process having e.g. 5 extraction steps yielding 5 extracts, to treat one or more of the said extracts enzymatically, and combine the said one or more enzymatically treated extracts with one or more of the non-treated extracts. For example, a portion of the second and fifth extracts can be treated enzymatically (separately or combined) and blended with portions of the first and third non-treated extracts. Any combination of treated and non-treated extracts is possible to give such an envisaged blend.

The preparation of a gelatine extract or series of extracts may be carried out in a batch or continuous process. The process may further comprise other steps such as demineralisation, filtration, enzymatic hydrolysis treatment steps.

In an embodiment, step c) comprises blending of a plurality of enzymatically treated extracts of step b) with the corresponding series of gelatine extracts of step a), from which said plurality of enzymatically treated extracts were obtained. This means that in case of a series of e.g. five extracts, portions of the first and third extracts are enzymatically treated and combined with portions of the said first and third non-treated extracts. Again, said treated and non-treated extracts can be blended in any desirable proportions.

It is also possible to blend an enzymatically treated extract with a plurality of extract from a series of gelatine extracts, or to blend a plurality of enzymatically treated extracts with a single gelatine extract from such a series.

In an embodiment, at least one of the gelatine extracts of step a) of the process according to the invention has a viscosity higher than 3.0 mPa·s, preferably higher than 3.5 mPa·s, wherein said viscosity is measured on a 6.67 wt. % aqueous solution at 60° C.

The enzymatically treated extract is obtained by treating one or a series of gelatine extracts with one or more endoproteases. In contrast to exopeptidases which cut peptide bonds from the end-positioned amino acids in a protein structure, endoproteases cut peptides bonds inside a protein structure, and cleave proteins into smaller protein fragments or peptides. Therefore, an enzymatic treatment with one or more exoproteases would lead to a high number of free amino acids when degrading a protein, whereas an enzymatic treatment with one or more endoproteases would produce a high number of protein fragments and peptides.

Examples of suitable endoproteases are known to the skilled person. The conditions for the enzymatic treatment are preferably chosen such, that the viscosity of the extract is decreased, while keeping the bloom value thereof substantially intact. The skilled person knows the conditions to apply to decrease the viscosity but to keep the bloom value, or can easily determine the conditions and enzyme choice without undue burden. Examples of proteases are: alcalase, neutrase, collagenase, serine protease, esperase, glutamyl endopeptidase, peptidase K protease, elastase, thermolysin, pepsin and neprilysin. By controlling the pH, temperature, and reaction time and enzyme choice of the enzymatic treatment, the desired enzymatically treated gelatine extract is obtained; i.e. an enzymatically treated extract with decreased viscosity, without significant impact on the bloom value and comprising less than 1.5 w/w % of gelatine-derived peptides having a molecular weight of less than 2000 Da, preferably an enzymatically treated extract comprising less than 1.5 w/w % of gelatine-derived peptides having a molecular weight of between 100 and 2000 Da.

The gelatine extract or series of gelatine extracts of step a) can be obtained by treatment of one or more gelatine-comprising raw materials under alkaline or acidic conditions. The one or more gelatine comprising raw materials can be obtained from one or more sources selected from the group consisting of bovine, porcine, fish, poultry, sheep and goat. The starting material for the extraction process according to the present invention may be a source that is the by-product of the meat industry. Preferably, the raw material is selected from the groups consisting of bovine, porcine, poultry and fish, more preferably bovine, porcine and poultry, most preferably bovine.

In an embodiment, the one or more gelatine-comprising raw materials are raw materials obtained from bone, hide, skin, cartilage, tissue and mixtures thereof. The inventive process is not limited to a particular raw material source. Preferably the raw material is selected from the group consisting of bone, hide, skin and mixtures thereof. Bone, hide and skin are sources of type I collagen. In another preferred embodiment, the cartridge is used as the raw material source. Cartilage is a source of type II collagen.

Preferably, the one or more gelatine-comprising raw materials are selected from the group consisting of bovine bone, bovine hide, porcine bone, porcine skin and fish skin.

In an embodiment, the gelatine-comprising raw material is subjected to an alkaline treatment step, said raw material being selected from the group consisting bovine bone, bovine hide, and porcine bone. It has been found that alkaline treatment of bovine bones, bovine hides and porcine bones yields a gelatine composition that is particularly desirable.

Alternatively, the gelatine comprising raw material is subjected to an acid treatment step, said raw material being selected from the group consisting of bovine bone, bovine hide, porcine skin and fish skin.

In another embodiment, the gelatine comprising raw material is subjected to an alkaline and acid treatment step, said raw material being selected from the group consisting bovine bone, bovine hide, porcine bone, porcine skin, fish bone and fish skin and mixtures thereof.

In an embodiment the gelatine extract or series of gelatine extract is obtained from a single gelatine-comprising raw material.

In another embodiment, the gelatine blend obtained in step d) of the method according to the invention, has a viscosity of between 2.0-3.5 mPa·s and a bloom of between 135-200 g, preferably between 145-175 g, when the gelatine blend is obtained from one or more gelatine extracts derived from a gelatine-comprising raw material treated under alkaline conditions, or a viscosity of between 1.8-3.3 mPa·s and a bloom of between 150-300 g, preferably between 160-280 g, when the gelatine blend is obtained from one or more gelatine extracts derived from a gelatine-comprising raw material treated under acidic conditions, or a viscosity of between 2.0-3.1 mPa·s and a bloom of between 180-220 g, when the gelatine blend is obtained from one or more gelatine extracts derived from a gelatine-comprising raw material treated under alkaline conditions and from a gelatine-comprising raw material treated under acidic conditions, wherein the viscosity is measured on a 6.67% wt. % aqueous solution at 60° C. and the bloom on a 6.67% aqueous solution at 10° C.

In an embodiment, step a) comprises the further step of monitoring the viscosity of the one or more gelatine extracts of step a), such that when the gelatine-comprising raw material has been treated under alkaline conditions and the viscosity of at least one of the gelatine extracts is more than 3.0 mPa·s said one or more gelatine extracts is blended with the one or more enzymatically treated extracts, so that a gelatine blend having a viscosity of between 2.0 and 3.5 mPa·s and a bloom of 135-200 g, preferably between 145-175 g, is obtained.

In an embodiment, step a) comprises the further step of monitoring the viscosity of the one or more gelatine extracts of step a), such that when the gelatine-comprising raw material has been treated under acidic conditions and the viscosity of one of the gelatine extracts is more than 3.0 mPa·s, said one or more gelatine extracts is blended with the one or more enzymatically treated extracts, so that a gelatine blend having a viscosity of between 1.8-3.3 mPa·s and a bloom of 150-300 g, preferably between 160-280 g, is obtained.

In an embodiment, step a) comprises the further step of monitoring the viscosity of the one or more gelatine extracts of step a), such that when the gelatine-comprising raw material has been treated under acid and alkaline conditions and the viscosity of one of the gelatine extracts is more than 3 mPa·s, for example more than 3.5 mPa·s, said one or more gelatine extracts is blended with the one or more enzymatically treated extracts so that a gelatine blend having a viscosity of between 2.0-3.1 mPa·s, and a bloom of 180-220 g, preferably between 190-210 g is obtained.

It has been found that, when the viscosity of the one or a series of gelatine extracts is found to be above 3.0 mPa·s, preferably above 3.5 mPa·s, the viscosity of the one or a series of gelatine extracts can be reduced by blending with one or more enzymatically treated extract to arrive at a composition having a lower viscosity. This results in a gelatine composition having a lower viscosity than the gelatine composition prior to blending with the one or more enzymatically treated extract. This has the advantage that the viscosity can be lowered, but the bloom is not adversely affected.

Another advantage of the present invention is that the gelatine blend may comprise gelatine extracts obtained from different extraction processes or that have undergone different treatments conditions, for example acid or alkaline treatment conditions. By monitoring the viscosity of the resultant composition obtainable by blending at least two gelatine extracts, which may each be provided as a product from different processes, it is possible to obtain a gelatine blend that exhibits a lower ability to form crosslinks, yet is easily processed into capsules, for example soft gelatine capsules. At least one of said at least two gelatine extracts refers to an enzymatically treated extract having a viscosity that is lower than that of the respective extract before said enzymatic treatment, while maintaining the bloom substantially unaffected; the enzymatically treated extracts comprising less than 1.5 w/w % of gelatine derived peptides having a molecular weight of less than 2000 Da.

Yet another advantage of the present invention is that the reduction in viscosity is achieved without adding free, that is being substantially free of, amino acids or peptides having a molecular weight of about 100 to about 2000 Da. By substantially free is meant that the blend comprises less than 1.5 wt. % of components having a molecular weight of less than 2000 Da, preferably between 100 and 2000 Da. The physiochemical properties (elasticity, gel strength, setting or gelling and film forming) are therefore not adversely affected, as may be the case when free amino acids or peptides are added to gelatine compositions, as is done in the prior art, in order to reduce cross-linking when such gelatines are used in capsules.

Cross-linking in the context of the present invention is the result of chemical reactions in the capsules where covalent bonds are formed between gelatine polypeptide chains and/or with reactive moieties in the filling of the capsule. Chemicals (e.g. aldehydes, dyes) or environmental factors (temperature, light, and humidity) can cause cross-linking. Amino acids lysine and arginine in the gelatine may also be attacked by e.g. an aldehyde. Cross-linking makes the gelatine insoluble. Cross-linking is discussed in "Cross-linking of gelatine capsules and its relevance to their in vitro-in vivo performance", Dignes et al, J. Pharmaceutical Sciences, 1994, 83, 7, and herein incorporated by reference.

It is therefore possible for the first time to prepare a gelatine composition, i.e. a gelatine blend having a reduced viscosity but in which the bloom is not significantly reduced, and low molecular weight amino acids and peptides are present in a small amount (i.e. less than 1.5 wt. %), thereby the gelling properties of the gelatine are not adversely affected.

"Viscosity" in the context of the present invention means the dynamic viscosity, expressed in mPa·s when tested as a 6.67% solution in water at 60° C. The viscosity of a 6.67% solution of gelatine may be determined at 60° C. by measuring the flow time of 100 ml of the solution through a standard pipette according to the GME Monograph Standardised Methods for the Testing of Edible Gelatine [11 Jan. 2015] The viscosity of any sample (V) with the efflux time t may be calculated from the equation:

$$V = (A \times t - B/t) \times d$$

where V=dynamic viscosity in mPa·s
For gelatine at 6.67%, 60° C. d=1.001
t=flowtime in seconds and 1/00 seconds
d=mass-volume of the gelatine solution in g/cm$^3$ at 60° C.µ
6.67% gelatine solution at 60° C.–d=1.001
12.5% gelatine solution at 60° C.–d=1.03
20% ASF-solution at 25° C.–d=1.060
A & B=pipet constants:

|   | 0300VIP01 | 0300VIP02 |
|---|-----------|-----------|
| A | 1.2706    | 1.1718    |
| B | 517.88    | 500.07    |

"Bloom" in the context of the present invention means the mass in grams necessary to depress a standard plunger 4 mm into the gel having a concentration of 6.67% and matured at 10.0° C. for 17 h, in other words, the gel strength. Bloom may be determined using a 6.67% solution of a gelatine sample prepared in a wide-mouthed test bottle at 60° C., cooled to 10.0° C. and kept for 17 h for maturation at this temperature, which is then tested using a gelometer, according to the GME Monograph Standardised Methods for the Testing of Edible Gelatine [11, Jan. 2015].

"pH" in the context of the present invention is a number, which represents conventionally the hydrogen ion concentration of an aqueous solution. The pH of a 6.67% gelatine solution can be determined by potentiometry at a temperature of 55-60° C. using a pH meter. The pH may also be determined on a 1% solution at 55° C. as described in the European pharmacopoeia [8$^{th}$ edition, 2014].

The molecular weight of the peptides and free amino acids is determined from plots of the molecular weight distribution of the samples. Molecular weight distribution is determined with high performance size exclusion chromatography. The column used is TSKgel PWXL precolumn+GMPWXL+G4000SWXL columns (Tosho Bioscience), the buffer used is a phosphate based buffer with 1% SDS set at pH 5.3. Separated molecules are detected by an UV-detector at a wavelength of 210 nm.

Typically an alkaline gelatine has a bloom of between 135-200 g, preferably between 145-175 g, and a viscosity of between 3.6-4.2 mPa·s. Surprisingly, it has been found that by monitoring the viscosity during the blending process of step d), i.e. blending of at least one or more gelatine extracts with one or more enzymatically treated extracts, different extracts can be combined to provide, a gelatine composition that has a surprisingly low viscosity of between 2.0-3.5 mPa·s, while the bloom remains between 135-200 g, preferably between 145-175 g.

A gelatine produced by alkaline hydrolysis (limed) is known as a type B gelatine. A type B gelatine bovine bone/hide has a bloom of about 135-200 g, for example between 145-175 g, and a viscosity of between 3.6-4.2 mPa·s. In an embodiment, the viscosity of a type B bovine bone/hide gelatine is between 2.0-3.5, preferably between 2.1-3.3, more preferably between 2.2-3.2 mPa·s.

Likewise, for acid gelatines and alkaline/acid gelatines, the viscosity of the gelatine composition obtained in the process according to the invention is lower than the standard viscosity for a comparable gelatine. For example, an acid gelatine having a bloom of about 160-205 g, for example between 170-195 g, has a viscosity of between 2.2-3.0 mPa·s (standard gelatine type A bovine bone) whereas the corresponding gelatine according to the invention has a viscosity of between 1.8-2.2 mPa·s. A gelatine produced by acid hydrolysis is known as a type A gelatine.

In an embodiment, the viscosity of a type A bovine bone gelatine is between 1.8-2.2, preferably between 1.9 and 2.1, more preferably between 2.0 and 2.1 mPa·s.

An acid gelatine such as a gelatine type A derived from bovine hide can have a bloom of between 165-215 g and a viscosity of between 2.7-3.2 mPa·s whereas the corresponding gelatine blend according to the invention has a viscosity of between 1.8-2.6 mPa·s.

In an embodiment, the viscosity of a gelatine blend from gelatine extracts derived from type A bovine hide gelatine is between 1.8-2.6, preferably between 2.0-2.4 mPa·s, more preferably between 2.1-2.3 mPa·s.

In an embodiment, the gelatine composition comprises gelatine extracted from different raw materials, for example from alkaline bovine hide and bovine bone. A gelatine composition comprising bovine bone and bovine hide has a bloom of about 135-200 g, preferably 145-175 g, and a viscosity of 3.6-4.2 mPa·s. It has been found that by using the process of the present invention; i.e. by blending the one or more gelatine extracts with one or more enzymatically treated extracts, the viscosity of a gelatine composition comprising bovine bone and bovine hide can be reduced to 2.0-3.5 mPa·s when the bloom is 135-200 g; for example, between 145-175 g.

It is possible to combine a first gelatine extract resulting from an acidic treatment with a second gelatine extract resulting from an alkali treatment. Subsequently, these combined gelatines can be blended with an enzymatically treated extract to produce a gelatine blend, wherein said gelatine blend has a viscosity of between 2.0-3.1 mPa·s as measured on a 6.67% wt. % aqueous solution at 60° C., a pH of between 4.5 and 7.0, and a bloom of between 180-220 g, preferably between 190-210 g, as measured on a 6.67 wt. % aqueous solution at 10° C., said blend comprising less than 1.5 wt. % of free amino acids and peptides having a molecular weight between 100 and 2000 Da. The portion of a gelatine extract used for preparing the enzymatically treated gelatine extract can be a gelatine extract resulting from an acidic treatment and/or an alkali treatment.

In an embodiment, the gelatine composition, i.e. blend, comprises gelatine extracted from a single gelatine-comprising raw material, for example from bovine hide but that has been subjected to both acidic and alkaline treatment steps. In another embodiment, the gelatine composition comprises one or more gelatine extracts from bovine hide that has been subjected to acidic treatment and one or more gelatine extracts from bovine hide that has been subjected to alkaline treatment. An example of standard gelatine compositions comprising bovine hide that has been treated under both acidic and alkaline conditions and gelatine compositions comprising one or more gelatine extracts from bovine hide that has been subjected to acidic treatment and one or more gelatine extracts from bovine hide that has been subjected to alkaline treatment has a bloom of about 180-220g, for example between 190-210g and a viscosity of about 3.2-4.2 mPa·s, for example, between 3.2-4.2 mPa·s. It has been found that by using the process of the present invention; i.e. by blending one or more gelatine extracts with one or more enzymatically treated extracts, the viscosity of a gelatine composition comprising bovine hide that had previously been treated under acidic and alkaline conditions and that of a gelatine composition comprising one or more gelatine extracts from bovine hide that have been subjected to acidic treatment and one or more gelatine extracts from bovine hide that have been subjected to alkaline treatment can be reduced to about 2.0-3.1 mPa·s, when the bloom is between 180-220 g.

Yet another example of the present invention relates to pig (porcine) derived gelatines. For example, an acid pig skin gelatine having a bloom of between 150 g-220 g, has a viscosity of about 2.6-3.4 mPa·s (standard gelatine type A pig skin) whereas the corresponding gelatine blend according to the invention has a viscosity of between 1.8-2.5 mPa·s.

In an embodiment, the viscosity of a gelatine blend prepared from extracts derived from type A porcine bone gelatine is between 1.8-2.5 mPa·s, preferably between 1.9-2.4 mPa·s, more preferably between 2.0-2.3 mPa·s.

Yet another utility of the present invention is in the production of gelatine from fish skin. For example an acid fish skin gelatine having a bloom of about 180 g-220 g, preferably between 190-210 g, has a viscosity of between 3.6-4.2 mPa·s (standard gelatine type A fish skin 200g) whereas the corresponding gelatine blend according to the invention has a viscosity of between 1.8-3.5 mPa·s. In a further example, an acid fish skin gelatine having a bloom of about 245 g -295 g, for example between 255-280 g, has a viscosity of between 3.3-4.3 mPa·s (standard gelatine type A fish skin 275 g) whereas the corresponding gelatine blend according to the invention has a viscosity of between 1.8-3.2 mPa·s.

In an embodiment, the method further comprises the steps of:
  e1) of measuring the pH of the blended gelatine blend of step d),
  e2) adjusting the pH to be:
    between 4.9-5.2, preferably between 5.0-5.2, more preferably between 5.0-5.1, if the pH measured in step e1) is above 5.3, and when the gelatine composition is obtained from a gelatine-comprising raw material treated under alkaline conditions,
    between 4.3-5.5, preferably between 4.5-5.3, more preferably between 4.7-5.2, if the pH measure in step e1) is above 5.6, and when the gelatine composition is obtained from a gelatine-comprising raw material treated under acidic conditions,
    between 4.5-5, preferably 4.7-5, if the pH measure in step e1) is above 5.0, and when the gelatine composition is obtained from a gelatine-comprising raw material treated under alkaline conditions and a gelatine-comprising raw material treated under acidic conditions.

The pH can be adjusted by adding, for example, an acid to the gelatine composition, or by blending one or more gelatine extracts having different pH.

In an embodiment, the pH of the resultant gelatine composition is lowered relative to the standard gelatines as defined herein, on the proviso that for acid gelatines the minimum pH is 4.3, for alkaline gelatines the minimum pH is 4.9, and for gelatine composition obtained from a gelatine-comprising raw material treated under alkaline conditions and a gelatine-comprising raw material treated under acidic conditions, the minimum pH is 4.5.

It has been found that lowering the pH of the gelatine composition, i.e. blend, obtained from blending one or more gelatine extracts is with one or more enzymatically treated extracts, does not adversely affect the gel strength or viscosity but further reduces the cross-linking of the gelatine composition towards reactive groups, such as aldehydes. Surprisingly, decreasing the pH of, for example, an alkaline bovine bone gelatine having a viscosity of 3.3 mPa·s from pH 5.6 to pH 5.3 leads to a reduced propensity for cross-links to form between the gelatine composition and formaldehyde.

In another embodiment, the process further comprises the step e) of adding between 0.01 and 10 wt. % ammonium salt, based on the total weight of the composition, to the gelatine composition of step c) or d). Examples of ammonium salts are: ammonium chloride, ammonium sulphate, ammonium acetate, di-ammonium hydrogen phosphate and tri-ammonium citrate. The quantity of ammonium salt added will vary depending on the nature of the solubility and the concentration of substances to be encapsulated. In general, between 2-100 g of ammonium salt per kg of gelatine, relative to the dry mass of gelatine, is added. For example from preferably 4-80 g, more preferably 5-70g.

The inventors have also found that adding an ammonium salt to the gelatine composition leads to a reduction in the propensity of the gelatine composition according to the invention to form cross-links with reactive groups such as aldehydes. The addition of ammonium salt does not adversely affect the gel strength or viscosity of the gelatine composition.

The gelatine composition obtainable by the process of the present invention having a lower viscosity and lower pH than a standard gelatine of the same bloom value is therefore particularly suited to be used in applications where cross-linking is problematic, for example in the manufacture of soft gelatine capsules.

The gelatine composition obtainable by the process described herein has good processability due to its lower viscosity, relative to standard gelatines of the same bloom.

In a second aspect, the present application relates to a gelatine composition comprising an alkaline gelatine having a bloom of between 135-200 g, and a viscosity of between 2.0-3.5 mPa·s, the gelatine composition preferably having
- a bloom of between 175-200 g and a viscosity of between 2.0-3.5 mPa·s, or
- a bloom of between 150-175 g and a viscosity of between 2.0-3 mPa·s, or
- a bloom of between 135-150 g and a viscosity of between 2.0-2.5 mPa·s, wherein the viscosity is measured on a 6.67% wt. % aqueous solution at 60° C., and the bloom is measured on a 6.67 wt. % aqueous solution at 10° C.,
wherein said gelatine composition has a pH of between between 4.9-5.2, preferably between 5.0-5.2, more preferably between 5.0-5.1; and
wherein said gelatine composition comprises less than 1.5 wt. % of free amino acids and peptides having a molecular weight of less than 2000 Da.
gelatine composition obtainable by the process according to the present invention, as defined herein.

It has been found that a gelatine composition comprising an alkaline gelatine having such a low bloom and having a viscosity of between 2.0-3.5 mPa·s, has a reduced cross-linking than a gelatine having a viscosity of more than 3.5 mPa·s but the same bloom, that is a bloom of between 135-200 g.

In a third aspect, the present invention relates to a gelatine composition comprising an acid gelatine having a bloom of between 150-300 g, and a viscosity of between 1.8-3.3 mPa·s, the gelatine composition preferably having:
- a bloom of between 250-300 g and a viscosity of between 1.8-3.3 mPa·s; or a bloom of between 210-250 g and a viscosity of between 1.8-2.8 mPa·s; or a bloom of between 150-210 g and a viscosity of between 1.8-2.5 mPa·s; wherein the viscosity is measured on a 6.67% wt. % aqueous solution at 60° C., and the bloom is measured on a 6.67 wt. % aqueous solution at 10° C., wherein said gelatine composition has a pH of between between 4.3-5.5, preferably between 4.5-5.3, more preferably between 4.7-5.2; and wherein said gelatine composition comprises less than 1.5 wt. % of free amino acids and peptides having a molecular weight of less than 2000 Da.

It has been found that a gelatine composition, i.e. blend, comprising an acid gelatine having such a low bloom and having a viscosity of between 1.8-3.3 mPa·s, has a reduced cross-linking than a gelatine having a viscosity of more than 3.3 mPa·s but the same bloom, that is a bloom of between 150-300 g.

In a fourth aspect, the present invention relates to a gelatine composition, i.e. blend, comprising an alkaline and an acid gelatine having a bloom of between 180-220 g, and a viscosity of between 2.0-3.1 mPa·s; wherein the viscosity is measured on a 6.67% wt. % aqueous solution at 60° C., and the bloom is measured on a 6.67 wt. % aqueous solution at 10° C.; wherein said gelatine composition has a pH of between between 4.5-5.0, preferably 4.7-5.0; and wherein said gelatine composition comprises less than 1.5 wt. % of free amino acids and peptides having a molecular weight of less than 2000 Da.

It has been found that a gelatine composition, i.e. blend, comprising an alkaline and an acid gelatine having such a low bloom and having a viscosity of between 2.0-3.1 mPa·s, has a reduced cross-linking than a gelatine having a viscosity of more than 3.1 mPa·s but the same bloom, that is a bloom of between 180-220 g.

The following embodiments are applicable to all aspects of the present invention unless it is specifically stated that the embodiments relate to a specific aspect of the invention.

It has been found that a gelatine composition, i.e. blend, comprising an alkaline and/or acid derived gelatine, having a viscosity of between 1.8-3.5 mPa·s, a pH of between 4.3-5.5, and a bloom of between 135-300 g as measured on a 6.67 wt. % aqueous solution at 10° C., displays a reduced propensity for forming cross-linking on storage due to hot and humid conditions and/or towards reactive moieties such as aldehydes. Consequently, the gelatine compositions of the present invention have improved dissolution properties which is beneficial when such a gelatine composition is used in a gelatine product, such as a pharmaceutical or nutraceutical soft capsule.

Without wishing to be bound by theory, the reactivity of gelatine appears to arise from the trifunctional amino acids it contains, specifically lysine. In type B gelatine, the lysine derived ε-amino function content is typically 33.0 moles per gelatine molecule of 1,000 amino acid residues. The highly basic guanidino group of arginine is protonated at neutral pH and is thought to only be reactive at high pH.

Several pathways for cross-linking may occur. In some cases, cross-linking of the lysine residues present in the gelatine itself may occur. On storage, lysine residues proximal to each other are oxidatively deaminated to yield terminal aldehyde groups. One of these aldehyde groups may then be attacked by free ε-amino of a neighbouring lysine amino acid, subsequently leading to a series of aldol type reactions to produce a cross-linked product containing pyridinium rings. Such cross-linking may occur on storage of hard gelatine capsules.

Another type of cross-linking may occur when the amino group of a lysine amino acid reacts with an aldehyde present in the fill of a capsule, for example trace quantities of formaldehyde are found in corn starch which is a common excipient in many drug formulations. Also, plasticizers and preservatives, fats and polyethylenated compounds such as polyethylene glycol, ethers of polyethyleneglycol and aliphatic alcohols or phenols and non-ionic surfactants (polysorbates, esters of unsaturated fatty acids) can undergo autooxidation to form aldehydes of higher molecular weights which in turn react with the gelatine to form cross-links. This type of cross-linking takes place in soft capsules, but is usually absent in hard capsules.

Glucose or other aldose sugars (saccharides) are often also included in drug formulations and may provide another possibility for cross-linking. The aldehyde functional groups of these saccharides may react with the free ε-amine group of lysine to give an imine intermediate, which through an Amadori rearrangement produces a keto sugar, which in turn reacts with another ε-amine (lysine) in the gelatine to form a cross-linked gelatine.

The cross-links may form within one polypeptide strand of a gelatine molecule (intramolecular), or form between stands (intermolecular). Cross-links may form under high humidity conditions. The cross-linking forms a water-insoluble, rubbery membrane (pellicle) within a gelatine capsule, which membrane acts as a barrier to drug release and causes a decrease in the dissolution of the capsule.

It has been found that the gelatine compositions according to the present invention are less prone to forming cross-links with aldehydes than standard type A and type B gelatines.

In an embodiment, the gelatine is selected from the group of bovine, porcine, fish, poultry, sheep and goat gelatine.

The source of gelatine may be selected form the group of bone, hide, skin, cartilage, tissue gelatine and mixtures thereof.

In an embodiment, the gelatine is an alkaline bovine bone, alkaline bovine hide gelatine or an alkaline porcine bone gelatine, preferably an alkaline bovine bone gelatine. It has been found that an alkaline derived gelatine according to the present invention has a lower propensity for cross-linking than a standard type B gelatine.

In an embodiment, the gelatine is an acid bovine bone, acid bovine hide, an acid porcine skin gelatine, or an acid skin gelatine, preferably an acid porcine skin gelatine. It has been found that an acid derived gelatine according to the present invention has a lower propensity for cross-linking than a standard type A gelatine.

In an embodiment, the gelatine composition further comprises between 0.01 and 10 wt. % ammonium salt based on the total weight of the gelatine composition. Examples of ammonium salts are: ammonium chloride, ammonium sulphate, ammonium acetate, di-ammonium hydrogen phosphate and tri-ammonium citrate. The quantity of ammonium salt added will vary depending on the nature of the solubility and the concentration of substances to be encapsulated. In general, between 2-100 g of ammonium salt per kg of gelatine, relative to the dry mass of gelatine, is added. For example from preferably 4-80 g, more preferably 5-70 g.

It has been found that inclusion of an ammonium salt to the gelatine composition leads to a reduction in the propensity of the gelatine composition according to the invention to form cross-links with reactive groups such as aldehydes. The addition of ammonium salt does not adversely affect the gel strength or viscosity of the gelatine composition.

In an embodiment, the gelatine has a molecular weight of between 50,000 Da-200,000, preferably between 50,000-180,000 Da. The gelatine of the present invention composition is substantially free from free amino acids and peptides, said peptides having an average molecular weight between 100 and 2000 Da. By substantially free is meant that the composition comprises less than 1.5 wt. % of components having a molecular weight of between 100 and 2000 Da. In contrast the gelatine compositions of the prior art, the present invention achieves a reduction in cross-linking by limiting the viscosity of the gelatine to, for example, between 2.2-3.2 for a type B gelatine.

A further advantage of the present invention is that when the reduced viscosity gelatine composition is incorporated in a gelatine product such as a capsule, for example a soft capsule, a reduction is observed in the amount of cross-linking in the gelatine capsule that is induced by the fill.

In a fifth aspect, the present invention relates to a gelatine product comprising a gelatine composition as defined herein or obtainable by a process according to the invention, said product preferably being selected from the group consisting of film, capsule, casing or coating.

The inventors have found that the gelatine composition according to the present invention is advantageous for the preparation of gelatine products, such as films, capsules, casings and coatings. In an embodiment, the product is a capsule.

Capsules are of particular relevance in the pharmaceutical and nutraceutical industries. It is known that gelatine used to make capsules, for example hard and soft gelatine capsules, may undergo chemical changes on storage as a result of cross-links forming between gelatine strands, typically in hard gelatine capsules, or between the fill and the gelatine shell, typically in soft capsules. The result of the reaction between a gelatine shell and the liquid contents is known as a "pellicle". Within the context of the present invention, a pellicle means a relatively water-insoluble membrane formed in a gelatine capsule shell wherein the membrane tends to be thin, tough, and rubbery.

The present invention provides a gelatine that is less prone to forming cross-links. Consequently, the present invention offers a solution to the problem of pellicle formation in soft gelatine capsules. Moreover, the present invention provides a solution to the problem of intermolecular cross-links in hard gelatine capsules.

Reduced cross-linking in capsules can be studied in a model system in which the viscosity of a gelatine solution in the presence of an aldehyde is monitored over time. An increase in viscosity is indicative of crosslinking.

Alternatively cross-linking may be determined by an altered dissolution profile. Accordingly, quantification of dissolution rate of a capsule can be determined by comparison of the dissolution profile of a capsule within a reasonably short time after capsule preparation and of a second capsule after storage under stressed conditions (e.g. four weeks at 40° C. and 85% relative humidity in a closed container) as described herein provides one means of assessing pellicle formation and/or gelatine cross- linking. The term "within a reasonably short time after capsule formation" means within a period of time such that substantial cross-linking and/or pellicle formation is unlikely to have yet occurred, for example within one week, dependent upon storage condition during that period. The term "pellicle resistant" herein means that such a gelatine capsule so described has a reduced tendency to form, or exhibits slowed, delayed or reduced formation of a pellicle upon storage under stressed conditions. Similarly, "inhibition of cross-linking" (or "inhibition of pellicle formation") herein means a slowed, delayed or reduced formation of gelatine cross-links (or pellicle formation) by comparison with an amount a similar capsule lacking the gelatine composition as provided herein.

In an embodiment, the capsule is a hard or soft gelatine capsule, preferably a soft gelatine capsule. Capsules are solid dosage forms in which the drug substance and/or excipients are enclosed within a soluble container or shell or coated on the capsule shell. The shells may be composed of two pieces (a body and a cap), or they may be composed of a single piece. Two-piece capsules are commonly referred to as hard-shell capsules, and one-piece capsules are often referred to as soft-shell capsules. This two piece and one-piece capsule distinction reflect differing levels of plasticizers in the two compositions and the fact that one-piece capsules typically are more pliable than two-piece capsules.

Capsules according to the invention are intended for oral administration. In an embodiment, the capsules are immediate-release capsules, that is there is no prolonged release.

Gelatine capsule shells normally contain between 6% and 16% water. The shells may be manufactured in one set of operations and later filled in a separate manufacturing process. Two-piece shell capsules are made by a process that involves dipping shaped pins into gelatine or hypromellose solutions, followed by drying, cutting, and joining steps. Powder formulations for two-piece gelatine capsules generally consist of the drug substance and at least one excipient. Liquid formulations may also be used. Both the formulation and the method of filling can affect release of the drug substance. In the filling operation, the body and cap of the shell are separated before filling. Following the filling operation, the machinery rejoins the body and cap and ensures satisfactory closure of the capsule by exerting appropriate force on the two pieces. The joined capsules can be sealed after filling by a band at the joint of the body and cap or by a designed locking joint between the cap and body. In compounding prescription practice, two-piece capsules may be hand-filled. This permits the prescriber the choice of selecting either a single drug substance or a combination of drug substances at the exact dose level considered best for an individual patient.

One-piece capsules are typically used to deliver a drug substance as a solution or suspension. Liquid formulations placed into one-piece capsules may offer advantages by comparison with dry-filled capsules and tablets in achieving content uniformity of potent drug substance(s) or acceptable dissolution of drug substance(s) with poor aqueous solubility. The gelatine of the present invention is particularly suited to such liquid filled capsules because despite the contact between the shell wall and its liquid contents there is a reduction in undesired interactions between the shell and the fill, compared to prior art gelatines.

One-piece capsules are formed, filled, and sealed in a single process on the same machine and are available in a wide variety of sizes, shapes, and colours. The most common type of one piece capsule is that produced by a rotary die process that results in a capsule with a seam. The soft gelatine shell is somewhat thicker than that of two-piece capsules and is plasticized by the addition of polyols such as glycerin, sorbitol, or other suitable materials. The ratio of the plasticizer to the gelatine can be varied to change the flexibility of the shell depending on the nature of the fill material, its intended usage, or environmental conditions. In most cases, one-piece capsules are filled with liquids. Typically, drug substances are dissolved or suspended in a liquid vehicle. Classically, an oleaginous vehicle such as a vegetable oil was used. However, non-aqueous, water-miscible liquid vehicles such as the lower molecular weight polyethylene glycols are now more common. The physicochemical properties of the vehicle can be chosen to ensure stability of the drug substance as well as to influence the release profile from the capsule shell.

Capsules according to the present invention define a fill volume and such fill volume can be occupied at least partially by any fill material. The fill material can comprise any active drug. Preferably, the active drug is a drug of low water solubility, also referred to herein as a poorly water soluble drug. A "drug of low water solubility" or "poorly water solubility drug" herein refers to any drug or compound having a solubility in water, measured at 37° C., not greater than about 10 mg/ml, and preferably not greater than about 1 mg/ml. Particularly preferred drugs having a solubility in water, measured at 37° C., not greater than about 0.1 mg/ml.

Solubility in water for many drugs can be readily determined from standard pharmaceutical reference books, for example The Merck Index, 11th ed., 1989 (published by Merck & Co., Inc., Rahway, N.J.); the United States Pharmacopoeia, 24th ed. (USP 24), 2000; The Extra Pharmacopoeia, 29th ed., 1989 (published by Pharmaceutical Press, London); and the Physicians Desk Reference (PDR), 2001 ed. (published by Medical Economics Co., Montvale, N.J.).

For example, individual drugs of low solubility as defined herein include those drugs categorized as "slightly soluble", "very slightly soluble", "practically insoluble" and "insoluble" in USP 24, pp. 2254-2298; and those drugs categorized as requiring 100 ml or more of water to dissolve 1 g of the drug, as listed in USP 24, pp. 2299-2304. Illustratively, suitable drugs of low water solubility include, without limitation, drugs from the following classes: abortifacients, ACE inhibitors, α- and β-adrenergic agonists, —and β-adrenergic blockers, adrenocortical suppressants, adrenocorticotropic hormones, alcohol deterrents, aldose reductase inhibitors, aldosterone antagonists, anabolics, analgesics (including narcotic and non-narcotic analgesics), androgens, angiotensin II receptor antagonists, anorexics, antacids, anthelminthics, antiacne agents, antiallergics, antialopecia agents, antiamebics, antiandrogens, antianginal agents, antiarrhythmics, antiarteriosclerotics, antiarthritic/antirheumatic agents (including selective COX-2 inhibitors), antiasthmatics, antibacterials, antibacterial adjuncts, anticholinergics, anticoagulants, anticonvulsants, antidepressants, antidiabetics, antidiarrheal agents, antidiuretics, antidotes to poison, antidyskinetics, antieczematics, antiemetics, antiestrogens, antifibrotics, antiflatulents, antifungals, antiglaucoma agents, antigonadotropins, antigout agents, antihistaminics, antihyperactives, antihyperlipoproteinemics, antihyperphosphatemics, antihypertensives, antihyperthyroid agents, antihypotensives, antihypothyroid agents, anti-inflammatories, antimalarials, antimanics, antimethemoglobinemics, antimigraine agents, antimuscarinics, antimycobacterials, antineoplastic agents and adjuncts, antineutropenics, antiosteoporotics, antipagetics, antiparkinsonian agents, antipheochromocytoma agents, antipneumocystis agents, antiprostatic hypertrophy agents, antiprotozoals, antipruritics, antipsoriatics, antipsychotics, antipyretics, antirickettsials, antiseborrheics, antiseptics/disinfectants, antispasmodics, antisyphylitics, antithrombocythemics, antithrombotics, antitussives, antiulceratives, antiurolithics, antivenins, antiviral agents, anxiolytics, aromatase inhibitors, astringents, benzodiazepine antagonists, bone resorption inhibitors, bradycardic agents, bradykinin antagonists, bronchodilators, calcium channel blockers, calcium regulators, carbonic anhydrase inhibitors, cardiotonics, CCK antagonists, chelating agents, cholelitholytic agents, choleretics, cholinergics, cholinesterase inhibitors, cholinesterase reactivators, CNS stimulants, contraceptives, debriding agents, decongestants, depigmentors, dermatitis herpetiformis suppressants, digestive aids, diuretics, dopamine receptor agonists, dopamine receptor antagonists, ectoparasiticides, emetics, enkephalinase inhibitors, enzymes, enzyme cofactors, estrogens, expectorants, fibrinogen receptor antagonists, fluoride supplements, gastric and pancreatic secretion stimulants, gastric cytoprotectants, gastric proton pump inhibitors, gastric secretion inhibitors, gastroprokinetics, glucocorticoids, glucosidase inhibitors, gonad-stimulating principles, growth hormone inhibitors, growth hormone releasing factors, growth stimulants, hematinics, hematopoietics, hemolytics, hemostatics, heparin antagonists, hepatic enzyme inducers, hepatoprotectants, histamine H2 receptor antagonists, HJN protease inhibitors, HMG CoA reductase inhibitors, immunomodulators, immunosuppressants, insulin sensitizers, ion exchange resins, keratolytics, lactation stimulating hormones, laxatives/cathartics, leukotriene antagonists, LH-RH agonists, lipotropics, 5-lipoxygenase inhibitors, lupus erythematosus suppressants, matrix metalloproteinase inhibitors, mineralocorticoids, miotics, monoamine oxidase inhibitors, mucolytics, muscle relaxants, mydriatics, narcotic antagonists, neuroprotectives, nootropics, ovarian hormones, oxytocics, pepsin inhibitors, pigmentation agents, plasma volume expanders, potassium channel activators/openers, progestogens, prolactin inhibitors, prostaglandins, protease inhibitors, radio-pharmaceuticals, 5α-reductase inhibitors, respiratory stimulants, reverse transcriptase inhibitors, sedatives/hypnotics, serenics, serotonin noradrenaline reuptake inhibitors, serotonin receptor agonists, serotonin receptor antagonists, serotonin uptake inhibitors, somatostatin analogs, thrombolytics, thromboxane A2 receptor antagonists, thyroid hormones, thyrotropic hormones, tocolytics, topoisomerase I and II inhibitors, uricosurics, vasomodulators including vasodilators and vasoconstrictors, vasoprotectants, xanthine oxidase inhibitors, and combinations thereof.

Non-limiting illustrative examples of suitable drugs of low water solubility include acetohexamide, acetylsalicylic acid, alclofenac, allopurinol, atropine, benzthiazide, cacprofen, celecoxib, chlordiazepoxide, chlorpromazine, clonidine, codeine, codeine phosphate, codeine sulphate, deracoxib, diacerein, diclofenac, diltiazem, estradiol, etodolac, etoposide, etoricoxib, fenbufen, fenclofenac, fenprofen, fentiazac, flurbiprofen, griseofulvin, haloperidol, ibuprofen, indomethacin, indoprofen, ketoprofen, lorazepam, medroxyprogesterone acetate, megestrol, methoxsalen, methylprednisone, morphine, morphine sulphate, naproxen, nicergoline, nifedipine, niflumic, oxaprozin, oxazepam, oxyphenbutazone, paclitaxel, phenindione, phenobarbital, piroxicam, piqrprofen, prednisolone, prednisone, procaine, progesterone, pyrimethamine, rofecoxib, sulfadiazine, sulfamerazine, sulfisoxazole, sulindac, suprofen, temazepam, tiaprofenic acid, tilomisole, tolmetic, valdecoxib, etc.

The amount of drug incorporated into fill material to be filled into a capsule of the invention can be selected according to known principles of pharmacy. A therapeutically effective amount of drug is specifically contemplated. The term "therapeutically and/or prophylactically effective amount" as used herein refers to an amount of drug that is sufficient to elicit the required or desired therapeutic and/or prophylactic response. Preferably, the therapeutic agent is present in an amount of at least about 0.01%, preferably at least about 0.1%, more preferably at least about 1%, and still more preferably at least about 5%, by weight of the fill material.

Fill material according to the invention optionally comprises one or more pharmaceutically acceptable sweeteners. Non-limiting examples of suitable sweeteners include mannitol, propylene glycol, sodium saccharin, acesulfame K, neotame and aspartame. Alternatively or in addition, a viscous sweetener such as sorbitol solution, syrup (sucrose solution) or high-fructose corn syrup can be used and, in addition to sweetening effects, can also be useful to increase viscosity and to retard sedimentation. Fill material of the invention optionally comprises one or more pharmaceutically acceptable preservatives other than free radical-scavenging antioxidants. Non-limiting examples of suitable preservatives include benzalkonium chloride, benzethonium chloride, benzyl alcohol, chlorobutanol, phenol, phenylethyl alcohol, phenylmercuric nitrate, thimerosal, etc.

Fill material of the invention optionally comprises one or more pharmaceutically acceptable wetting agents. Surfactants, hydrophilic polymers and certain clays can be useful as wetting agents to aid in dissolution and/or dispersion of a hydrophobic drug such as celecoxib. Non-limiting examples of suitable surfactants include benzalkonium chloride, benzethonium chloride, cetylpyridinium chloride, dioctyl sodium sulfosuccinate, nonoxynol 9, nonoxynol 10, octoxynol 9, poloxamers, polyoxyethylene (8) caprylic/capric mono- and diglycerides (e.g., Labrasol™ of Gattefosse), polyoxyethylene (35) castor oil, polyoxyethylene (20) cetostearyl ether, polyoxyethylene (40) hydrogenated castor oil, polyoxyethylene (10) oleyl ether, polyoxyethylene (40) stearate, polysorbate 20, polysorbate 40, polysorbate 60, polysorbate 80 (e.g., Tween™ 80 of ICI), propylene glycol laurate (e.g., Lauroglycol™ of Gattefosse), sodium lauryl sulphate, sorbitan monolaurate, sorbitan monooleate, sorbitan monopalmitate, sorbitan monostearate, tyloxapol, and mixtures thereof. Additionally, dosage forms of the invention optionally comprise one or more pharmaceutically acceptable buffering agents, flavouring agents, colorants, stabilizers and/or thickeners. Buffers can be used to control pH of a formulation and can thereby modulate drug solubility. Flavouring agents can enhance patient compliance by making the dosage form more palatable, and colorants can provide a product with a more aesthetic and/or distinctive appearance. Non-limiting examples of suitable colorants include D&C Red No. 33, FD&C Red No. 3, FD&C Red No. 40, D&C Yellow No. 10, and C Yellow No. 6.

In a sixth aspect, the present invention relates to the use of a gelatine composition as defined herein or obtainable by a process according to the invention in a film, capsule, casing or coating.

Pharmaceutical dosage forms according to the present invention have been found to exhibit an unexpected and surprisingly substantial reduction in cross- linking of the gelatine in the capsule shell and pellicle formation. As a result, such dosage forms are capable of consistently meeting desired in vitro dissolution criteria, even after storage under stressed conditions. This invention represents a significant improvement over conventional dosage forms and conventional gelatine capsule shells.

EXPERIMENTAL

Example 1

Bovine Bone Gelatine Compositions According to the Invention

Bovine bone (gelatine comprising raw material) was acidulated, washed and subjected to an alkaline treatment step. The washing are collected and gelatine is extracted from the treated bovine bone using hot water. For example in a multi-stage batch process, hot water with increasing temperature in each stage is used to extract gelatine; this temperature being comprised between 50° C. and 90° C. The bloom and viscosity of the gelatine decreases from the first to the last extraction step. In the present example, the bloom of the gelatine extracts ranges from 60-290g and viscosity is between 1.9-8 mPa·s. Additionally, an enzymatically treated extract is obtained by subjecting a portion of the gelatine extracts to an enzymatic treatment with an endoprotease as described above, resulting in lowering of the viscosity, but substantially retaining the bloom value. Gelatine compositions having blooms of about 140 g and about 180 g and a viscosity of between 2.0-3.5 mPa·s, are obtained by blending gelatine from different extractions with the enzymatically treated extract, while monitoring the viscosity of the gelatine composition. It is to be noted that the bloom of the enzymatically treated extract is similar to that of the corresponding extract before being subjected to the enzymatic treatment.

In the following examples a cross-linking test was used to determine how quickly the cross-linking reaction of gelatine with formaldehyde occurs. In this test the viscosity of a 20% gelatine solution in water is followed up over time after addition of 0.4 w/w % formaldehyde to the gelatine solution at 50° C. Viscosity is measured with a Brookfield LVDV2T equipment while maintaining the solution at 50° C. Following parameters are defined from the test results:

a) The Speed of the Cross-Linking Reaction

The percentage of viscosity increase is calculated for the different data points (only for viscosity values lower than 300 mPa·s) using the following formula:

$$\text{Viscosity increase at } t\ (\%) = \frac{(\text{Viscosity at } t0 - \text{Viscosity at } t)}{\text{Viscosity at } t0} \times 100$$

These results are plotted on a logarithmic scale over time. The $10^{th}$ logarithm is taken of the values of viscosity increase and this is plotted in a graph together with the reaction time. The equation corresponding to the linear curve of this plot of $\text{Log}_{10}$(viscosity increase) over the reaction time is as follows:

$$y = a \cdot x + b \text{ with } y = \text{Log}_{10}(\text{viscosity increase}) \text{ in \%}$$

x=Reaction time in min.
a=speed of the reaction in %/min.
The value for a is then multiplied by 60 to have the result of the reaction speed in %/h
The slope of the linear trend line corresponding to this curve is defined as the speed of the cross-linking reaction.

b) The Cross-Linking Time

This is defined as the first time point where the viscosity value is higher than 60,000 mPa·s.

TABLE 1

Results of the cross-linking test for gelatine compositions prepared according to the invention. Result per gelatine type is the average result taken from 2 or 3 repeated tests on each batch.

| Ex. | Sample description | Bloom (6.67% - 10° C.) (g) | Viscosity (6.67% - 60° C.) (mPa · s) | pH (6.67% - 45° C.) | Ammonium chloride (ppm) | Reaction speed (%/h) | Crosslinking time (min.) |
|---|---|---|---|---|---|---|---|
| 1.1 | LB 140 bloom | 144 | 2.41 | 5.11 | 18,700 | 1.5 | 67.0 |
| 1.2 | LB 180 bloom | 180 | 2.52 | 5.12 | 18,700 | 1.7 | 60.3 |

Example 2

Crosslinking Test

The effect of gelatine of the invention having a lower viscosity and lower pH compared to standard gelatine, with or without the presence of ammonium salts was tested on the cross-linking reaction. Table 2 shows the specifications of the batches used together with the test results, that are also shown in FIG. 1.

All samples used were 160 LB gelatine; i.e. a type B bovine bone gelatine having a bloom of about 160 g. These samples were prepared using a procedure similar as described for Example 1. The standard 160 LB gelatine, had a viscosity of between 3.6-4.2 mPa·s, in this specific case 3.70 mPa·s, and a pH of between 5.3-6.2, in this specific case 5.73.

Improved gelatine with lower viscosity and pH shows prolonged cross-linking time, even more when ammonium salts are added.

TABLE 2

Results of the cross-linking test for improved 160 LB gelatines with lower viscosity and pH compared to standard 160 LB gelatine.

| | | Batch specification | | | | Test results | |
|---|---|---|---|---|---|---|---|
| Ex. | Sample | Bloom (6.67% - 10° C.) (g) | Viscosity (6.67% - 60° C.) (mPa · s) | pH (6.67% - 45° C.) | Ammonium salt addition (ppm) | Reaction speed (%/h) | Crosslinking time (min.) |
| 2.1 | Standard 160 LB | 159 | 3.70 | 5.73 | 23,500 AS | 2.7 | 28.5 |
| 2.2 | 160 LB lower viscosity and lower pH | 153 | 2.50 | 5.14 | — | 2.4 | 43.3 |

TABLE 2-continued

Results of the cross-linking test for improved 160 LB gelatines
with lower viscosity and pH compared to standard 160 LB gelatine.

| | | Batch specification | | | Test results | |
|---|---|---|---|---|---|---|
| | | Bloom | Viscosity | | | |
| Ex. | Sample | (6.67% - 10° C.) (g) | (6.67% - 60° C.) (mPa · s) | pH (6.67% - 45° C.) | Ammonium salt addition (ppm) | Reaction speed (%/h) | Crosslinking time (min.) |
| 2.3 | 160 LB lower viscosity and lower pH + AS | 160 | 2.45 | 5.20 | 23,500 AS | 1.7 | 58.1 |
| 2.4 | 160 LB lower viscosity and lower pH + AC | 162 | 2.48 | 5.09 | 18,700 AC | 1.7 | 58.8 |

AS: ammonium sulphate
AC: ammonium chloride

Example 3

Comparison with Known Gelatines

Figure 2:
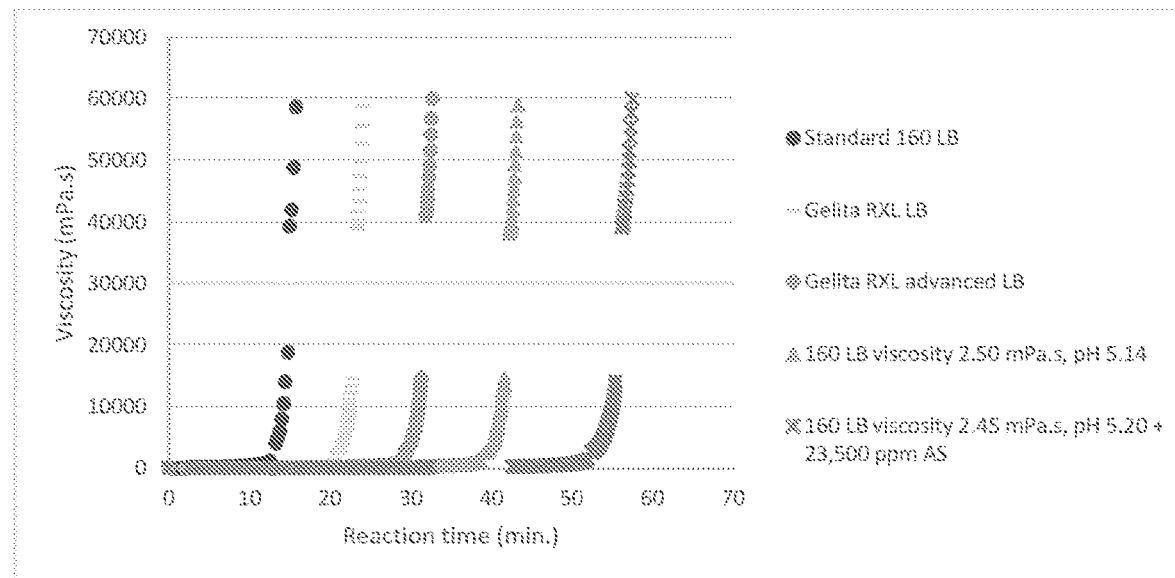
FIG. 2: Results of the cross-linking test for standard and improved 160 LB gelatines, comparison with a commercially available standard gelatine.
Black circles=standard 160 LB gelatine
Line=Gelita RXL LB gelatine
Grey circles=Gelita RXL advanced LB
Tringles=160 LB gelatine, viscosity 2.50 mPa·s. pH 5.14
Crosses=160 LB gelatine, viscosity 2.45 mPa·s, pH 5.20+ 23,500 ppm AS FIG. 3: molecular size distribution of known gelatines and according to the invention. Line with dots: 160 LB viscosity 2.50 mPa·s, pH 5.14; line with stripes: 160 LB viscosity 2.48 mPa·s, pH 5.09+18,700 ppm AC; solid line: Gelita RXL (bovine); line with stripes and dots: Gelita RXL advanced (bovine).

Comparison of gelatine composition according to the invention with commercially available "reduced cross-link gelatine", Gelita RXL and Gelita RXL advanced LB, both produced by Gelita AG, Germany. Referring to table 3 and FIG. 2, Gelita RXL and Gelita RXL advanced have a longer cross-linking time than standard 160LB, but the gelatine composition according to the invention having a lower viscosity has a longer cross-linking time than Gelita RXL. Addition of ammonium sulphate leads to a further improvement in cross-linking time. The effect has been doubled compared to Gelita RXL.

was determined with high performance size exclusion chromatography using a TSKgel PWXL precolumn+ GMPWXL+G4000SWXL columns (Tosho Bioscience) and a phosphate based buffer with 1% SDS set at pH 5.3. Separated molecules were detected by an UV-detector at a wavelength of 210 nm.

Figure 3:
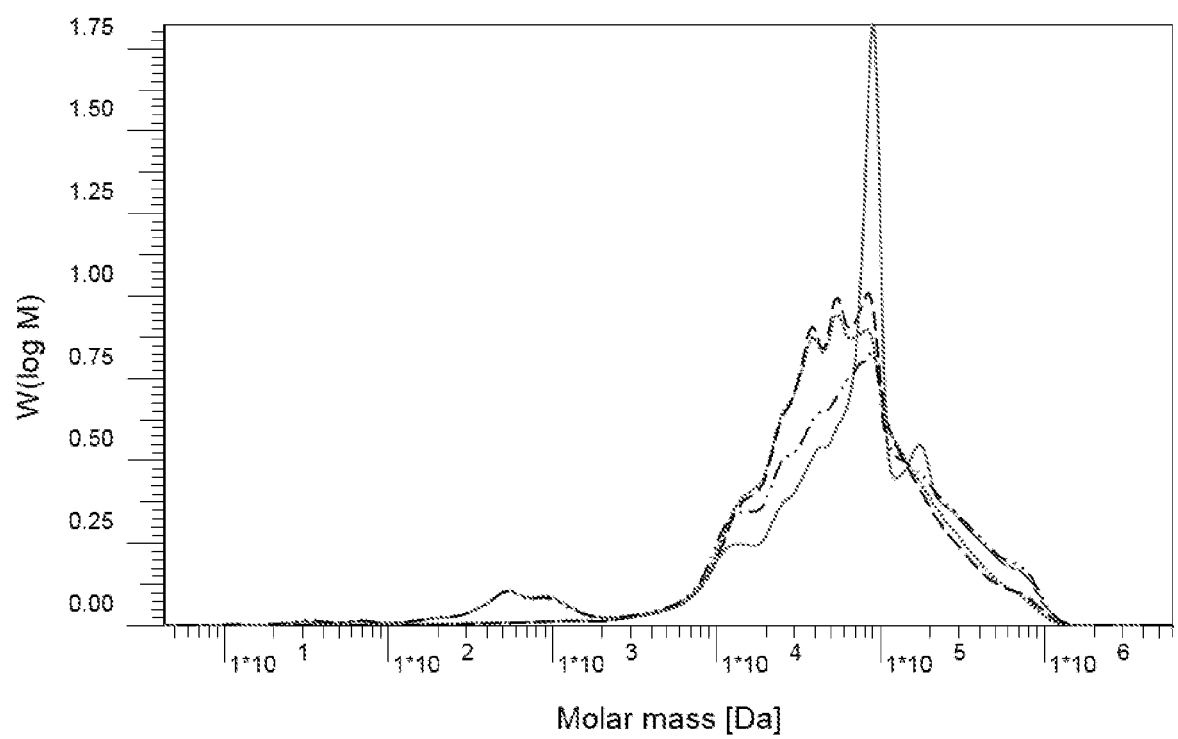

In FIG. 3, the molecular size distribution has been plotted, and it can clearly be seen that both gelatines of Gelita (solid line for Gelita RXL and the line with stripes and dots for Gelita RXL advanced) show significant presence of peptides having a molecular weight of between 100 and 1200 Da, which are absent in the standard 160 LB and the improved

TABLE 3

Results of the cross-linking test for standard and improved 160 LB

| | | Batch specification | | | | Test results | |
|---|---|---|---|---|---|---|---|
| | | Bloom | Viscosity | | | | |
| Ex. | Sample description | (6.67% - 10° C.) (g) | (6.67% - 60° C.) (mPa · s) | pH (6.67% 45° C.) | Ammonium sulphate (ppm) | Reaction speed (%/h) | Crosslinking time (min.) |
| 3.1 | Std. 160 LB | 159 | 3.70 | 5.73 | — | 6.0 | 15.8 |
| 3.2 | 160 LB lower viscosity and lower pH | 153 | 2.50 | 5.14 | — | 2.4 | 43.3 |
| 3.3 | 160 LB lower viscosity and lower pH + AS | 160 | 2.45 | 5.20 | 23,500 | 1.7 | 58.1 |
| 3.4 | Gelita RXL LB | 168 | 3.27 | 5.71 | — | 3.9 | 24.4 |
| 3.5 | Gelita RXL advanced LB | 145 | 2.69 | 5.64 | — | 3.3 | 32.8 |

Example 4

Molecular Weight Measurements

The molecular weight of the peptides and free amino acids was determined from plots of the molecular weight distribution of the samples. Molecular weight distribution gelatines of the invention (dotted line: 160 LB viscosity 2.50 mPa·s, pH 5.14; line with stripes: 160 LB viscosity 2.48 mPa·s, pH 5.09 +18,700 ppm AC). Further data are shown in table 4.

The presence of small peptides is disadvantageous as these peptides do not participate in the gelling process.

TABLE 4 molecular weight measurements

|  |  | Batch specification | | | Molecular weight results | | |
|---|---|---|---|---|---|---|---|
|  |  | | | | | Molecules <2000 Da | |
|  |  | Bloom | Viscosity | | | | |
| Ex. | Sample | (6.67% - 10° C.) (g) | (6.67% - 60° C.) (mPa · s) | pH (6.67% - 45° C.) | Ammonim chloride (ppm) | Average mol.wt. (Da) | Average mol.wt. (Da) | Wt % |
| 4.1 | 160 LB lower viscosity and lower pH | 153 | 2.50 | 5.14 | — | 103,250 | 810.91 | 1.04 |
| 4.2 | 160 LB lower viscostiy and lower pH + AC | 162 | 2.48 | 5.09 | 18,700 | 100,890 | 823.36 | 1.01 |
| 4.3 | Gelita RXL (bovine) | 168 | 3.27 | 5.71 | — | 128,150 | 703.03 | 6.10 |
| 4.4 | Gelita RXL advanced (bovine) | 145 | 2.69 | 5.64 | — | 100,790 | 694.29 | 7.11 |

Example 5

Pig Skin Gelatine Compositions According to the Invention

Pig skin (gelatine comprising raw material) was subjected to an acid treatment step. The washing are collected and gelatine is extracted from the treated pig skin using hot water. For example in a multi-stage batch process, hot water with increasing temperature in each stage is used to extract gelatine; this temperature being comprised between 50° C. and 90° C. Additionally, an enzymatically treated extract is obtained by subjecting a portion of the gelatine extracts to an enzymatic treatment with an endoprotease as explained above. Gelatine compositions a bloom of about 200 g (hereinafter "200 PS") and a viscosity of around 2.36 mPa·s are obtained by blending gelatine from different extractions with the enzymatically treated extract, while monitoring the viscosity of the gelatine composition. It should be noted that the bloom of the enzymatically treated extract is similar to that of the gelatine composition. The gelatine composition according to the invention is compared with a gelatine composition having a similar bloom but higher viscosity. This is shown in Table 5.

Example 6

Bovine Hide Gelatine Compositions According to the Invention

Bovine hide (gelatine comprising raw material) was subjected to a mixed acid and alkaline treatment step. The washings are collected and gelatine is extracted from the treated bovine hide using hot water. For example in a multi-stage batch process, hot water with increasing temperature in each stage is used to extract gelatine; this temperature being comprised between 50° C. and 90° C. Additionally, an enzymatically treated extract is obtained by subjecting a portion of the gelatine extracts to an enzymatic treatment with an endoprotease as explained above. Gelatine compositions a bloom of about 200 g (hereinafter "200 H") and a viscosity of around 2.99 mPa·s are obtained by blending gelatine from different extractions with the enzymatically treated extract, while monitoring the viscosity of the gelatine composition. It should be noted that the bloom of the enzymatically treated extract is similar to that of the gelatine composition.

The gelatine composition according to the invention is compared with a gelatine composition having a similar bloom but higher viscosity. This is shown in Table 6.

TABLE 5

Results of the cross-linking test for standard and improved 200 PS

| | | Batch specification | | | | Test results | |
|---|---|---|---|---|---|---|---|
| | | Bloom | Viscosity | | | | |
| Ex. | Sample description | (6.67% - 10° C.) (g) | (6.67% - 60° C.) (mPa · s) | pH (6.67% - 45° C.) | Ammonium sulphate (ppm) | Reaction speed (%/h) | Crosslinking time (min.) |
| 5.1 | Std. 200 PS | 206 | 2.94 | 5.24 | — | 3.0 | 36.1 |
| 5.2 | 200 PS lower viscosity & lower pH | 191 | 2.36 | 5.02 | — | 1.9 | 62.9 |
| 5.3 | 200 PS lower viscosity & lower pH + AS | 191 | 2.36 | 5.02 | 23,500 | 1.5 | 79.4 |

TABLE 6

Results of the cross-linking test for standard and improved 200 H

| | Batch specification | | | | Test results | |
|---|---|---|---|---|---|---|
| Ex. | Sample description | Bloom (6.67% - 10° C.) (g) | Viscosity (6.67% - 60° C.) (mPas) | PH (6.67% - 45° C.) | Ammonium sulphate (ppm) | Reaction speed (%/h) | Crosslinking time (min.) |
| 6.1 | Std. 200 H | 203 | 3.23 | 5.60 | — | 5.9 | 15.1 |
| 6.2 | 200 H lower viscosity & lower pH | 201 | 2.99 | 4.90 | — | 2.7 | 36.7 |
| 6.3 | 200 H lower viscosity & lower pH + AS | 201 | 2.99 | 4.90 | 23,500 | 2.3 | 44.6 |

Example 7

Processability Tests

The processability of gelatine compositions according to the invention was compared with the processability of a standard gelatine composition. To this aim soft capsules with 160 LB samples were prepared, see table 7. The processability is determined by using parameters such as thickness of the gelatine ribbon during capsule production, moisture content of a capsule shell, and seaming rate of capsules.

Thickness of gelatine ribbon was measured to be between 0.68 and 0.72 mm for all gelatines tested.

For moisture content determination, commonly prepared gelatine capsules were dried for 1.5 hours in a tumble dryer, followed by 7 days in 18-22° C. and 15-25% RH. The moisture content varied among the gelatines tested from 8 to 9.5%.

Seaming rate is the ratio of seam thickness on shell thickness. Upper seaming rate >50% for all gelatines tested. Disintegration was tested after 2 months at 25° C./50% RH conditions and at 30° C./62% RH. All gelatines tested comply with the specifications according to European Pharmacopeia 8.0. The results show that the gelatine according to the invention behave the same as a standard gelatine in the soft capsule production process.

TABLE 7

Samples used for the processablity tests

| | | Batch specification | | | |
|---|---|---|---|---|---|
| Ex. | Sample description | Bloom (6.67% - 10° C.) (g) | Viscosity (6.67% - 60° C.) (mPa·s) | pH (6.67% - 45° C.) | Ammonium salt ppm |
| 7.1 | Std. 160 LB | 164 | 3.78 | 5.58 | — |
| 7.2 | 160 LB lower viscosity & lower pH | 153 | 2.50 | 5.14 | — |
| 7.3 | 160 LB lower viscosity & lower pH + AS | 160 | 2.45 | 5.20 | 23,500 AS |
| 7.4 | 160 LB lower viscosity & lower pH + AC | 162 | 2.48 | 5.09 | 18,700 AC |

In summary, the examples show that lowering the viscosity of a gelatine composition according to the process of the present invention leads to a reduction in cross-linking compared to standard gelatines as indicated by the increased cross-linking time.

The present invention also provides a gelatine composition having a longer cross-linking time than a comparable commercially available Gelita RXL gelatine. The cross-linking time can also be further increased by addition of ammonium salt.

What is claimed is:

1. A process for the preparation of a gelatine blend comprising the steps of:
    a) providing a gelatine extract or a series of gelatine extracts, differing in bloom and viscosity,
    b) subjecting a portion of one or more of the gelatine extracts of step a) to an enzymatic treatment to obtain one or more enzymatically treated extracts having a viscosity that is lower than that of the respective extract before said enzymatic treatment, while maintaining the bloom substantially unaffected, the enzymatically treated extracts comprising less than 1.5 w/w % of gelatine-derived peptides having a molecular weight of less than 2000 Da, wherein said enzymatic treatment is carried out using one or more endoproteases,
    c) selecting one or more gelatine extracts of step a),
    d) combine the selected one or more gelatine extracts of step c) and blend with one or more enzymatically treated extracts of step b) to provide a gelatine composition having a lower viscosity as compared to that of the said combined selected extracts of step c) without being blended with said selected one or more enzymatically treated gelatine extracts of step b), while maintaining the bloom substantially unaffected.

2. The process according to claim 1, wherein step a) comprises the preparation of a series of extractions, wherein
    i. a first extraction step results in a first gelatine extract having a first viscosity and a first bloom, followed by,
    ii. a subsequent second extraction step resulting in a second additional gelatine extract having a second viscosity and a second bloom, optionally followed by,
    iii. one or more subsequent additional extraction steps, each resulting in a subsequent additional gelatine extract having a subsequent viscosity and a subsequent bloom.

3. The process according to claim 1, wherein at least one of the extracts of step a) has a viscosity higher than 3.0 mPa·s, wherein said viscosity is measured on a 6.67 wt. % aqueous solution at 60° C.

4. The process according to claim 1 wherein the gelatine extract or a series of gelatine extracts of step a) is obtained by treatment of one or more gelatine-comprising raw materials under alkaline or acidic conditions.

5. The process according to claim 4, wherein the one or more gelatine-comprising raw materials are obtained from one or more sources selected from the group consisting of bovine, porcine, fish, poultry, sheep and goat.

6. The process according to claim 1, wherein the gelatine blend obtained in step d) has
   a viscosity of between 2.0-3.5 mPa·s and a bloom of between 135-200 g, when the gelatine blend is obtained from one or more gelatine extracts derived from a gelatine-comprising raw material treated under alkaline conditions, or
   a viscosity of between 1.8-3.3 mPa·s and a bloom of between 150-300 g, when the gelatine blend is obtained from one or more gelatine extracts derived from a gelatine-comprising raw material treated under acidic conditions,
   or a viscosity of between 2.0-3.1 mPa·s and a bloom of between 180-220 g, when the gelatine blend is obtained from one or more gelatine extracts derived from a gelatine-comprising raw material treated under alkaline conditions and from a gelatine-comprising raw material treated under acidic conditions,
wherein the viscosity is measured on a 6.67 wt. % aqueous solution at 60° C. and the bloom on a 6.67 wt. % aqueous solution at 10° C.

7. The process according to claim 1, further comprising the steps of:
   e1) of measuring the pH of the gelatine blend of step d),
   e2) adjusting the pH to be:
      between 4.9-5.2, if the pH measured in step e1) is above 5.3, and when the gelatine blend is obtained from one or more gelatine extracts derived from a gelatine-comprising raw material treated under alkaline conditions,
      between 4.3-5.5, if the pH measure in step e1) is above 5.6, and when the gelatine blend is obtained from one or more gelatine extracts derived from a gelatine-comprising raw material treated under acidic conditions,
      between 4.5-5, if the pH measure in step e1) is above 5.0, and when the gelatine blend is obtained from one or more gelatine extracts derived from a gelatine-comprising raw material treated under alkaline conditions and a gelatine-comprising raw material treated under acidic conditions.

8. The process according to claim 7, wherein said process further comprises the step of:
   f) adding between 0.01 and 10 wt.-% ammonium salt, based on the total weight of the composition, to the gelatine blend of step d), e1) or e2).

9. A gelatine composition obtainable by the method of claim 1,
   wherein the gelatine composition has an increased cross-linking time as measured by the time point where the viscosity value is higher than 60,000 mPa·s in a 20% gelatine solution in water after addition of 0.4 w/w % formaldehyde to the gelatine solution at 50° C.

10. The gelatine composition according to claim 9, comprising an alkaline gelatine having a bloom of between 135-200 g, and a viscosity of between 2.0-3.5 mPa·s, wherein the viscosity is measured on a 6.67 wt. % aqueous solution at 60° C., and the bloom is measured on a 6.67 wt. % aqueous solution at 10° C., wherein said gelatine composition has a pH of between 4.9-5.2; and wherein said gelatine composition comprises less than 1.5 wt. % of free amino acids and peptides having a molecular weight of less than 2000 Da.

11. The gelatine composition according to claim 9, comprising an acid gelatine having a bloom of between 150-300 g, and a viscosity of between 1.8-3.3 mPa·s, wherein the viscosity is measured on a 6.67 wt. % aqueous solution at 60° C., and the bloom is measured on a 6.67 wt. % aqueous solution at 10° C., wherein said gelatine composition has a pH of between 4.3-5.5 and wherein said gelatine composition comprises less than 1.5 wt. % of free amino acids and peptides having a molecular weight of less than 2000 Da.

12. The gelatine composition according to claim 9, comprising an alkaline and an acid gelatine having a bloom of between 180-220 g, and a viscosity of between 2.0-3.1 mPa·s, wherein the viscosity is measured on a 6.67 wt. % aqueous solution at 60° C., and the bloom is measured on a 6.67 wt. % aqueous solution at 10° C., wherein said gelatine composition has a pH of between 4.5-5.0; and wherein said gelatine composition comprises less than 1.5 wt. % of free amino acids and peptides having a molecular weight of less than 2000 Da.

13. The gelatine composition according to claim 9, wherein said gelatine composition further comprises between 0.01-10 wt. % ammonium salt based on the total weight of the gelatine composition.

14. The gelatine composition according to claim 9, wherein said gelatine composition has an average molecular weight of between 50,000-200,000 Da.

15. The gelatine composition according to claim 10, wherein said gelatine composition is obtained by a process for the preparation of a gelatine blend comprising the steps of:
   a) providing a gelatine extract or a series of gelatine extracts, differing in bloom and viscosity,
   b) subjecting a portion of one or more of the gelatine extracts of step a) to an enzymatic treatment to obtain one or more enzymatically treated extracts having a viscosity that is lower than that of the respective extract before said enzymatic treatment, while maintaining the bloom substantially unaffected, the enzymatically treated extracts comprising less than 1.5 w/w % of gelatine-derived peptides having a molecular weight of less than 2000 Da,
   c) selecting one or more gelatine extracts of step a),
   d) combine the selected one or more gelatine extracts of step c) and blend with one or more enzymatically treated extracts of step b) to provide a gelatine composition having a lower viscosity as compared to that of the said combined selected extracts of step c) without being blended with said selected one or more enzymatically treated gelatine extracts of step b), while maintaining the bloom substantially unaffected.

16. The gelatine composition according to claim 11, wherein said gelatine composition is obtained by a process for the preparation of a gelatine blend comprising the steps of:
   a) providing a gelatine extract or a series of gelatine extracts, differing in bloom and viscosity,
   b) subjecting a portion of one or more of the gelatine extracts of step a) to an enzymatic treatment to obtain one or more enzymatically treated extracts having a viscosity that is lower than that of the respective extract before said enzymatic treatment, while maintaining the bloom substantially unaffected, the enzymatically treated extracts comprising less than 1.5 w/w % of gelatine-derived peptides having a molecular weight of less than 2000 Da,
   c) selecting one or more gelatine extracts of step a),
   d) combine the selected one or more gelatine extracts of step c) and blend with one or more enzymatically treated extracts of step b) to provide a gelatine composition having a lower viscosity as compared to that of the said combined selected extracts of step c) without being blended with said selected one or more enzymatically treated gelatine extracts of step b), while maintaining the bloom substantially unaffected.

17. The gelatine composition according to claim 12, wherein said gelatine wherein said gelatine composition is obtained by a process for the preparation of a gelatine blend comprising the steps of:
   a) providing a gelatine extract or a series of gelatine extracts, differing in bloom and viscosity,
   b) subjecting a portion of one or more of the gelatine extracts of step a) to an enzymatic treatment to obtain one or more enzymatically treated extracts having a viscosity that is lower than that of the respective extract before said enzymatic treatment, while maintaining the bloom substantially unaffected, the enzymatically treated extracts comprising less than 1.5 w/w% of gelatine-derived peptides having a molecular weight of less than 2000 Da,
   c) selecting one or more gelatine extracts of step a),
   d) combine the selected one or more gelatine extracts of step c) and blend with one or more enzymatically treated extracts of step b) to provide a gelatine composition having a lower viscosity as compared to that of the said combined selected extracts of step c) without being blended with said selected one or more enzymatically treated gelatine extracts of step b), while maintaining the bloom substantially unaffected.

18. The gelatine product comprising a gelatine composition according to claim 9, said product being selected from the group consisting of film, capsule, casing or coating.

19. A gelatine product comprising a gelatine composition obtainable by a process for the preparation of a gelatine blend comprising the steps of:
   a) providing a gelatine extract or a series of gelatine extracts, differing in bloom and viscosity,
   b) subjecting a portion of one or more of the gelatine extracts of step a) to an enzymatic treatment to obtain one or more enzymatically treated extracts having a viscosity that is lower than that of the respective extract before said enzymatic treatment, while maintaining the bloom substantially unaffected, the enzymatically treated extracts comprising less than 1.5 w/w % of gelatine-derived peptides having a molecular weight of less than 2000 Da, wherein said enzymatic treatment is carried out using one or more endoproteases,
   c) selecting one or more gelatine extracts of step a),
   d) combine the selected one or more gelatine extracts of step c) and blend with one or more enzymatically treated extracts of step b) to provide a gelatine composition having a lower viscosity as compared to that of the said combined selected extracts of step c) without being blended with said selected one or more enzymatically treated gelatine extracts of step b), while maintaining the bloom substantially unaffected,
   wherein the gelatine composition has an increased cross-linking time as measured by the time point where the viscosity value is higher than 60,000 mPa·s in a 20% gelatine solution in water after addition of 0.4 w/w % formaldehyde to the gelatine solution at 50° C.

* * * * *